United States Patent
Goldberg et al.

(10) Patent No.: US 7,190,275 B2
(45) Date of Patent: Mar. 13, 2007

(54) DRIP RATE MONITOR FOR INTRAVENOUS INFUSION SET

(76) Inventors: Barry A. Goldberg, 13882 N. Kendall Dr., Miami, FL (US) 33186; Shu Chung Lai, Suite 701-703 Wing on Plaza, 62 Mody Road, T.S.T. East, Kowloon, Hong Kong (HK)

( * ) Notice: Subject to any disclaimer, the term of this patent is extended or adjusted under 35 U.S.C. 154(b) by 484 days.

(21) Appl. No.: 10/704,436

(22) Filed: Nov. 7, 2003

(65) Prior Publication Data

US 2004/0171994 A1    Sep. 2, 2004

Related U.S. Application Data

(60) Provisional application No. 60/426,249, filed on Nov. 14, 2002.

(51) Int. Cl.
*G08B 21/00* (2006.01)

(52) U.S. Cl. .................. 340/606; 340/573.1; 604/253; 128/DIG. 13

(58) Field of Classification Search .................. 340/606
See application file for complete search history.

(56) References Cited

U.S. PATENT DOCUMENTS

| | | | |
|---|---|---|---|
| 4,432,761 A | | 2/1984 | Dawe |
| 4,509,943 A | | 4/1985 | Hanzawa |
| 4,551,134 A | * | 11/1985 | Slavik et al. .................. 604/67 |
| 4,623,331 A | * | 11/1986 | Cewers et al. ................. 604/65 |
| 4,718,896 A | * | 1/1988 | Arndt et al. ................. 604/253 |
| 5,045,069 A | | 9/1991 | Imparato |
| 5,211,626 A | * | 5/1993 | Frank et al. .................. 604/65 |
| 5,415,641 A | * | 5/1995 | Yerlikaya et al. ........... 604/251 |
| 5,609,576 A | * | 3/1997 | Voss et al. ..................... 604/67 |
| 5,899,665 A | * | 5/1999 | Makino et al. ................ 417/20 |
| 6,638,263 B1 | * | 10/2003 | Theeuwes et al. .......... 604/500 |

* cited by examiner

*Primary Examiner*—Daniel Wu
*Assistant Examiner*—George A. Bugg
(74) *Attorney, Agent, or Firm*—Gunster, Yoakley & Stewart, P.A.

(57) ABSTRACT

An apparatus for monitoring the drip rate of an infusion fluid being administered by an intravenous infusion set comprising a housing, drop sensor, alarm and processor. The housing is attachable to a drip chamber, and the drop sensor is positioned in the housing to detect drops of the infusion fluid being administered by the intravenous infusion set. The processor determines a first amount of time required for the drop sensor to detect a first set of drops of infusion fluid having a predetermined number of drops, determines a second amount of time required for the drop sensor to detect a second set of drops of infusion fluid having the predetermined number of drops, compares the second amount of time to a range of time having a minimum that is less than the first amount of time and a maximum that is greater than the first amount of time, and activates the alarm if the second period of time is not within the range of time.

13 Claims, 8 Drawing Sheets

DRIP RATE MONITOR FOR INTRAVENOUS INFUSION SET

CROSS-REFERENCE TO RELATED APPLICATION

This application is related to and claims priority to U.S. Provisional Application Ser. No. 60/426,249, filed Nov. 14, 2002, entitled METHOD AND APPARATUS FOR MONITORING VARIATIONS IN THE FLOW OF FLUIDS THROUGH AN ADMINISTRATION SET, the entirety of which is incorporated herein by reference.

STATEMENT REGARDING FEDERALLY SPONSORED RESEARCH OR DEVELOPMENT

Not Applicable

FIELD OF THE INVENTION

The invention relates generally to infusion systems, and more particularly, to a drip rate monitor for use with an intravenous infusion set.

BACKGROUND OF THE INVENTION

An intravenous infusion set is used to provide liquid intravenously to patients. An elevated drip-chamber is typically provided as part of a gravity feed administration set with tubing connected to the top and bottom of the chamber. The administrator of the fluids can control the flow of fluids by adjusting a clamp attached to the tubing that pinches the tubing thereby restricting the flow.

After the drip rate of the fluid is initially set, patient movement can adversely affect the flow. The tubing may become kinked by the patient rolling onto the tubing, thus reducing the flow of fluids. Excessive movement by the patient may cause changes to the resistance dynamics of the tubing causing a steady stream of fluid to pass through the tube into the drip-chamber rather than at the desired drip rate. Such changes in the flow of fluid when falling outside an acceptable range of drip rate variation can be dangerous to the patient, particularly when the change goes unnoticed for a length of time.

There are a number of devices that control the flow of fluids by mechanically adjusting the amount the tube is pinched based on a variety of factors. However, these devices are complicated, bulky and expensive. Further, if there is a mechanical malfunction or power source failure, there is no alarm to alert the administrator. Furthermore, none of the existing devices adequately alert the administrator of unacceptable variations in the drip rate of the fluids without first completely shutting down the flow. Accordingly, there is a need for a compact apparatus for monitoring and detecting unacceptable variations in the drip rate in a drip-chamber and alerting the administrator by sounding an audible signal.

SUMMARY OF THE INVENTION

In accordance with the present invention, there is provided an apparatus for monitoring the drip rate of an infusion fluid being administered by an intravenous infusion set. The apparatus comprises a housing, drop sensor, alarm and processor. The housing is attachable to a drip chamber, and the drop sensor is positioned in the housing to detect drops of the infusion fluid being administered by the intravenous infusion set. The processor determines a first amount of time required for the drop sensor to detect a first set of drops of infusion fluid having a predetermined number of drops, determines a second amount of time required for the drop sensor to detect a second set of drops of infusion fluid having the predetermined number of drops, compares the second amount of time to a range of time having a minimum that is less than the first amount of time and a maximum that is greater than the first amount of time, and activates the alarm if the second period of time is not within the range of time.

In addition, the present invention provides a portable apparatus for monitoring the drip rate of an infusion fluid being administered by an intravenous infusion set comprising a housing, flexible member for attaching the housing to a drip chamber of the intravenous infusion set, and a drop sensor positioned in the housing for detecting the drops in a drip chamber. The flexible member is detachable from the housing.

Still further the present invention provides a method of monitoring the drip rate of an infusion fluid being administered by an intravenous infusion set comprising the steps of detecting the drops of infusion fluid being administered by the intravenous infusion unit, determining a first amount of time required to detect a first set of drops of infusion fluid having a predetermined number of drops, determining a second amount of time required to detect a second set of drops of infusion fluid having the predetermined number of drops, comparing the second amount of time to a range of time having a minimum that is less than the first amount of time and a maximum that is greater than the first amount of time, and providing an alarm if the second period of time is not within the range of time.

Other advantages and applications of the present invention will be made apparent by the following detailed description of the preferred embodiment of the invention.

DETAILED DESCRIPTION OF THE INVENTION

Figure 1:
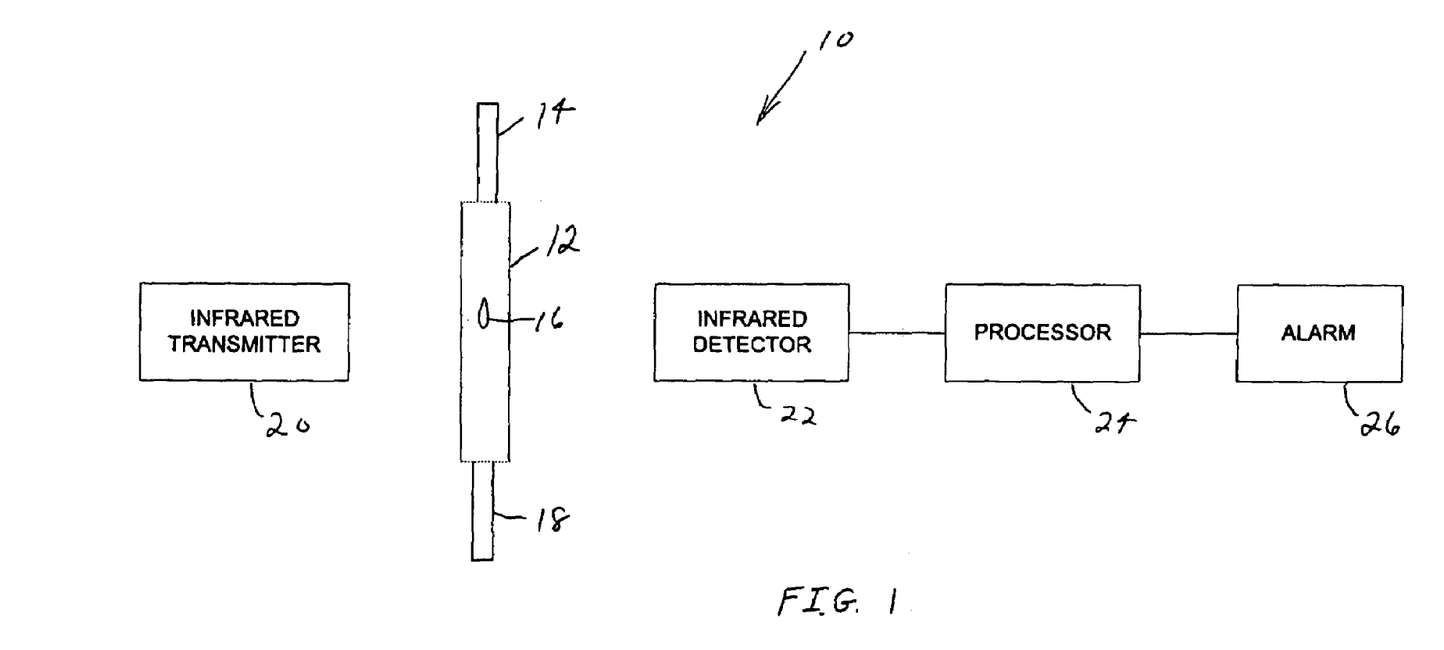
FIG. 1 is a schematic block diagram of a drip rate monitor according to one embodiment of the present invention.
Figure 2:
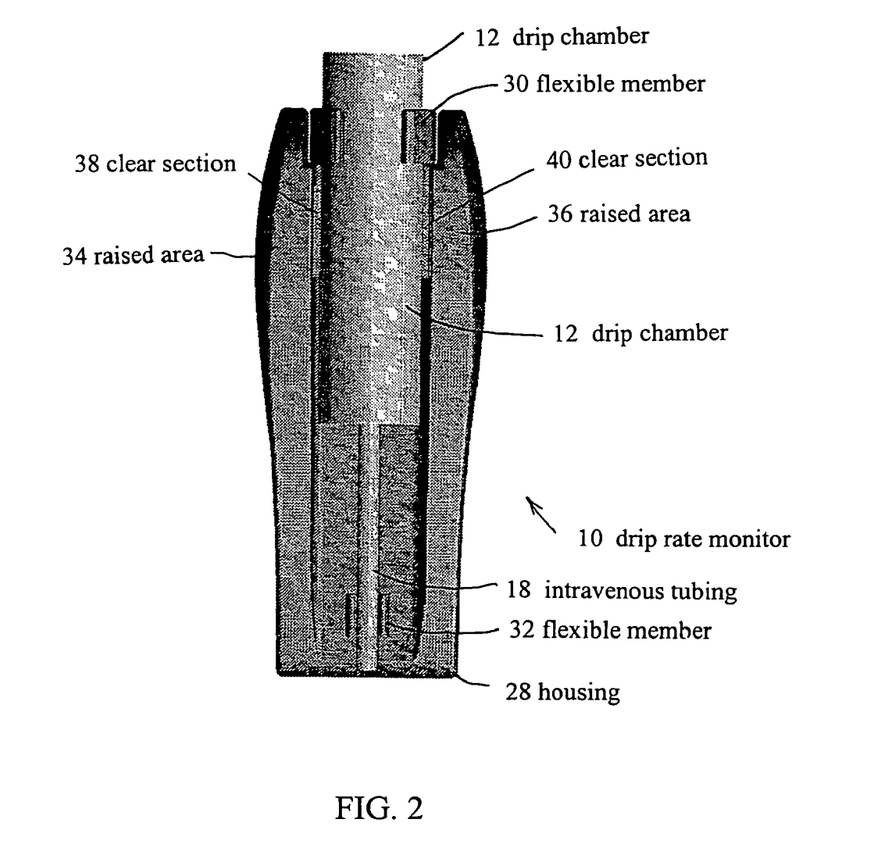
FIG. 2 is an elevational front view of a drip rate monitor according to one embodiment of the present invention.
Figure 3:
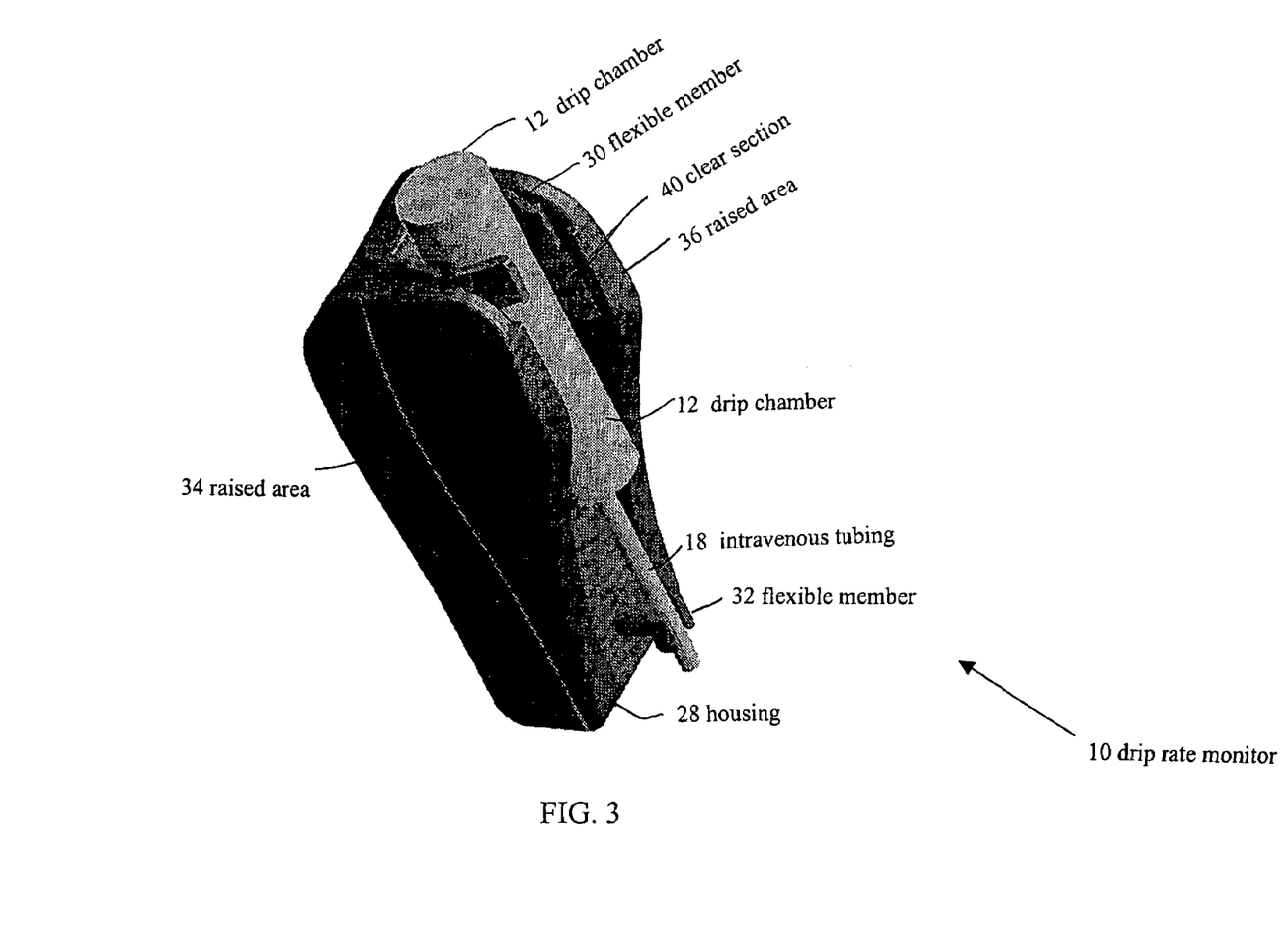
FIG. 3 is a perspective front view of the drip rate monitor shown in FIG. 2.
Figure 4:
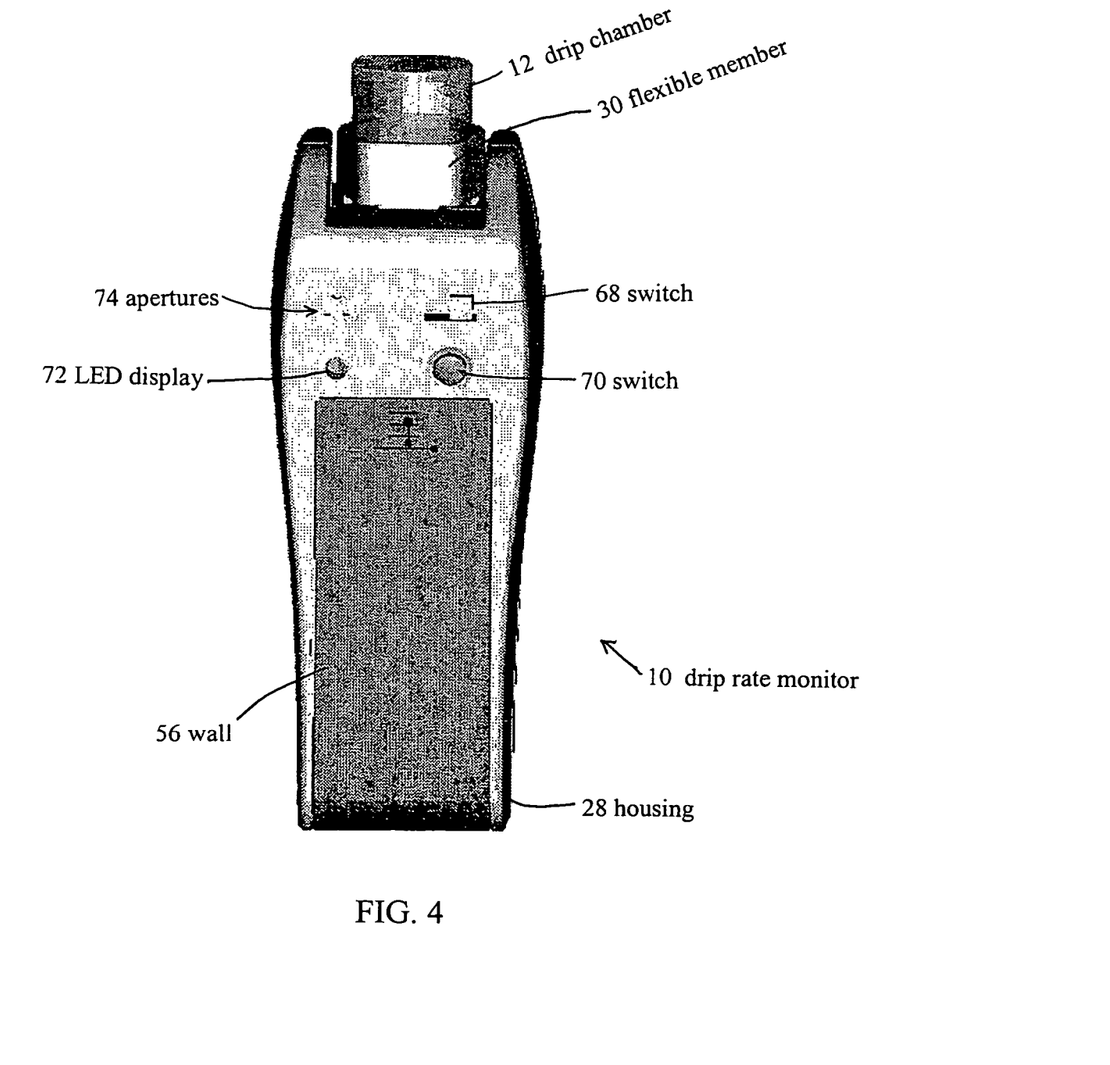
FIG. 4 is a perspective side view of the drip rate monitor shown in FIG. 2.
Figure 5:
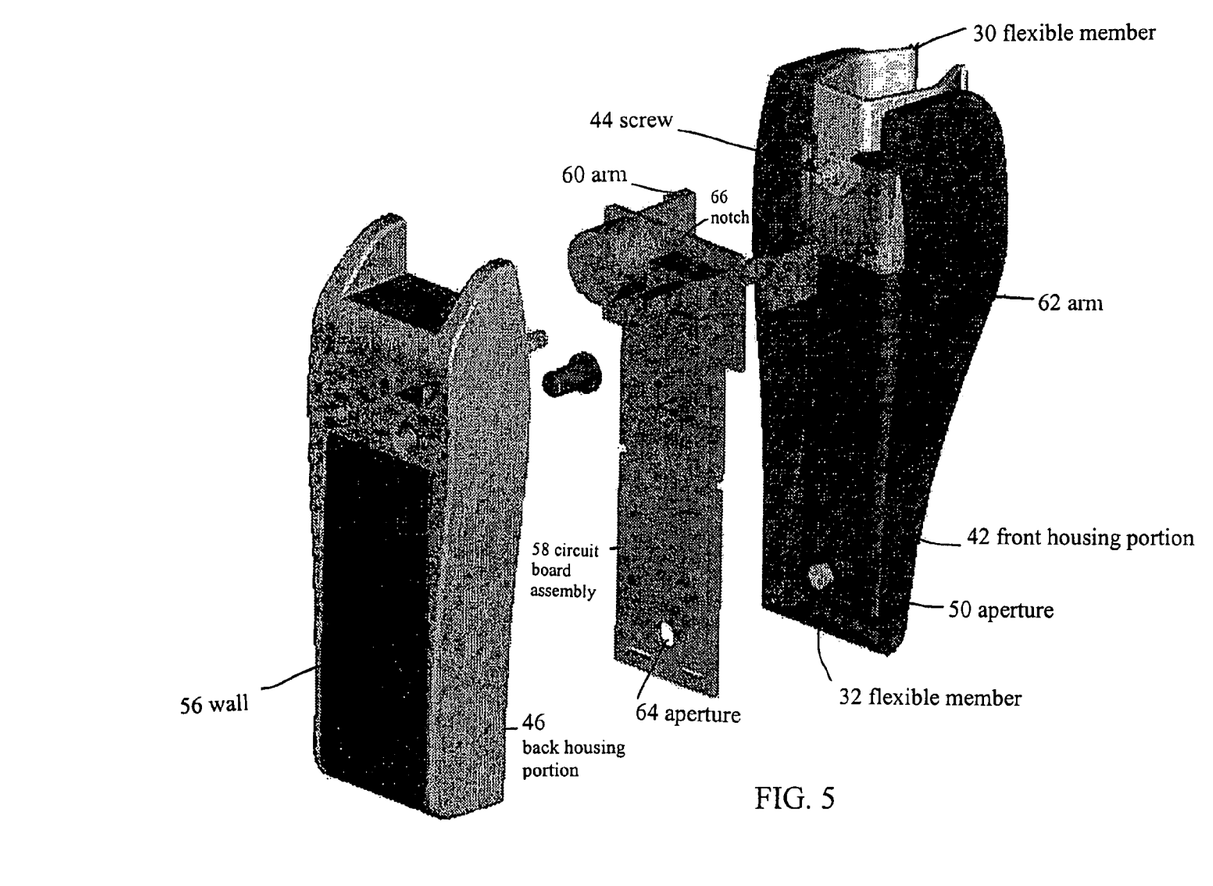
FIG. 5. is an exploded view of the drip rate monitor of the present invention.
Figure 6:
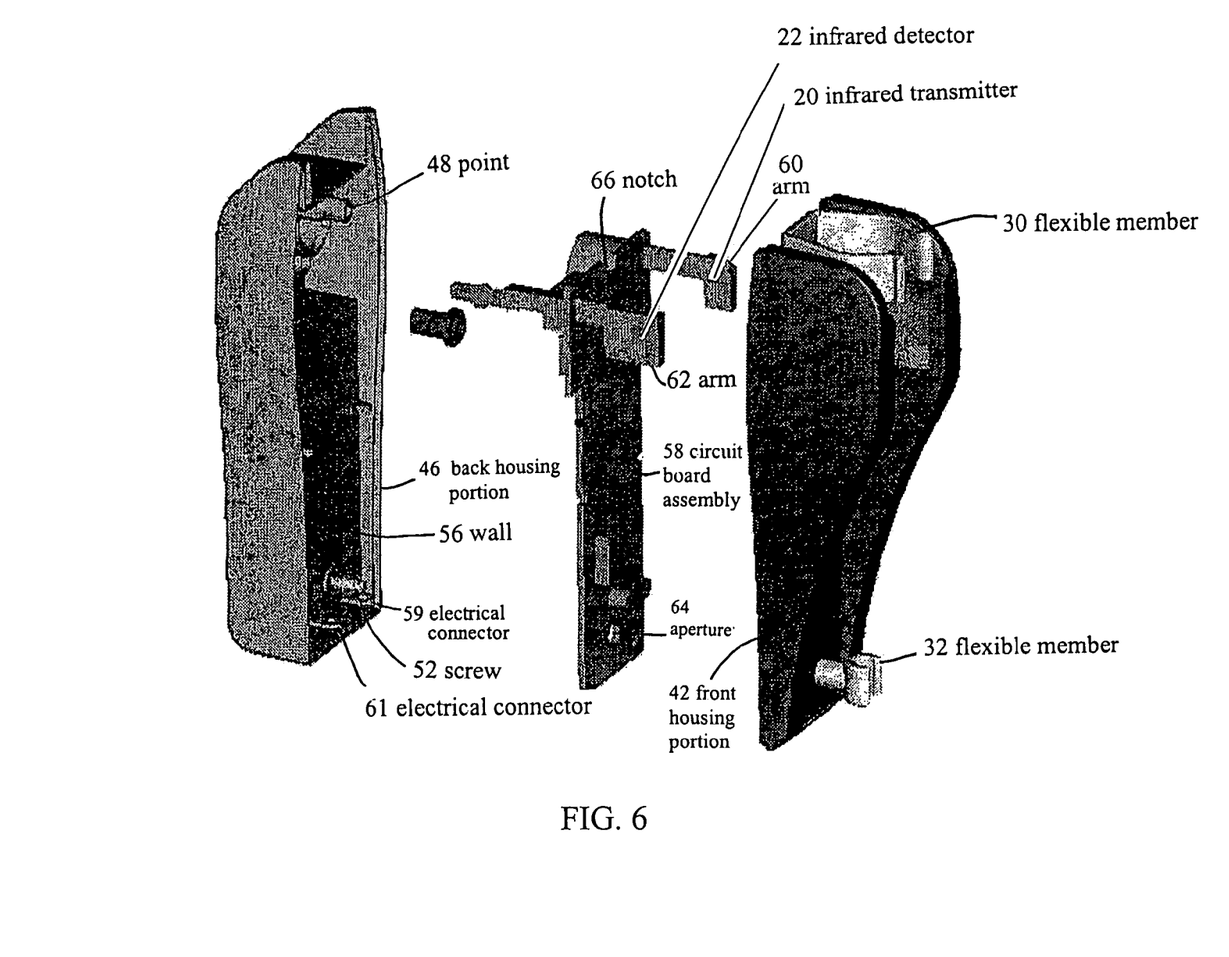
FIG. 6 is an exploded view of the drip rate monitor of the present invention.

Referring to FIG. 1, a drip rate monitor 10 for monitoring the drip rate of an infusion fluid being administered by an intravenous infusion set according to one embodiment of the invention is shown. A drip chamber 12, which can be for example a macro or micro drip chamber, is part of an intravenous infusion set as is known in the art. An infusion fluid is supplied to drip chamber 12 by tubing 14 a drop at a time as is shown by drop 16. The infusion fluid is provided to the patient by intravenous tubing 18. An infrared transmitter 20 and an infrared detector 22 are positioned on opposite sides of drip chamber 12 to detect drop 16 as it falls in drip chamber 12. When drip rate monitor 10 is in use, infrared transmitter 20 is always on and transmitting infrared light energy. The difference in the amount of infrared light energy received by infrared receiver 22 that occurs when drop 16 is in between infrared transmitter 20 and infrared transmitter 22, indicates the detection of a drop 16 of the infusion fluid. Infrared transmitter 20 can be a gallium-aluminum-arsenic infrared light-emitting diode, such as model number IE-430F, which is available form Waitrony Co. Limited. Infrared detector 22 can be an NPN silicon phototransistor, such as model number WPT-430F, which is available from Waitrony Co. Limited, and two such phototransistors can be located side-by-side to provide optimum resolution for drop rate determination since the drops can vary significantly in size. Although in the embodiment of the present invention shown in FIG. 1 drop 16 is sensed by using infrared transmitter 20 and infrared detector 22, other types of sensors can be used, for example, ultrasonic, CCD/CMOS imagers, and lasers. Infrared detector 22 can also include circuitry such as an operational amplifier operating in the comparative mode to compare the sensed signal with a predetermined reference signal to determine when a drip has occurred. The output from infrared detector 22 is provided to processor 24 which analyzes the drip rate and activates alarm 26 if the drip rate is outside of a set range as described in detail below with reference to FIG. 8. Alternatively, all or some portion of the steps performed by processor 24 can be implemented by discrete circuitry.

FIGS. 2–7 show the structure of drip rate monitor 10. Housing 28 is attached to drip chamber 12 by flexible member 30. Housing 28 can also have an additional flexible member 32 for attaching housing 28 to intravenous tubing 18 to provide additional security that housing 28 is properly positioned in relation to drip chamber 12. Housing 28, which can be made from, for example, a thermoplastic such as acrylonitrile butadiene styrene, has two raised areas 32 and 34 on opposite sides so that drip chamber 12 is located between raised areas 34 and 36. Flexible member 30 is positioned on housing 28 so that raised flexible member 30 is located inside of raised areas 34 and 36 to protect against accidental removal from drip chamber 12. Flexible member 30 is attached to housing 28 by a screw 44 that passes through flexible member 30 to hold flexible member 30 in position in front housing portion 42 and that screws into back housing portion 46 at point 48. A portion of flexible member 32 passes through aperture 50 in front housing portion 42. A screw 52 is positioned in an aperture in wall 56 of the battery compartment of back housing portion 46 and attaches flexible member 32 to housing 28. The head portion of screw 52 is located underneath lid 54 which covers the battery compartment. Flexible member 30 is flexible so that it can attach to both micro and macro drip chambers and be attached and removed many times. Suitable material for flexible member 30, as well as flexible member 32, is thermoplastic, such as polyacetal.

Each of raised areas 34 and 36 has a clear section 38 and 40 respectively so that infrared transmitter 20 can transmit infrared light through drip chamber 12 and infrared detector 22 can detect the transmitted infrared light. Clear sections 38 and 40 can be made of acrylic or other suitable clear material. A circuit board assembly 58, on which processor 24 and alarm 26 are mounted, is located inside housing 28. Circuit board assembly 58 has arms 60 and 62 on which infrared transmitter 20 and infrared detector 22 are mounted respectively. Arm 60 is positioned inside raised area 36 adjacent clear area 40, and arm 62 is positioned inside raised area 34 adjacent clear area 38. Circuit board assembly 58 has an aperture 64 through which screw 52 passes and a notch 66 that mates with point 48 to provide a configuration for easy assembly and rigid construction. Electrical connectors 61 and 63 extend from the battery chamber through wall 56 and connect to circuit board assembly 58 to provide power from the batteries (not shown) to circuit board assembly 58.

Figure 8:
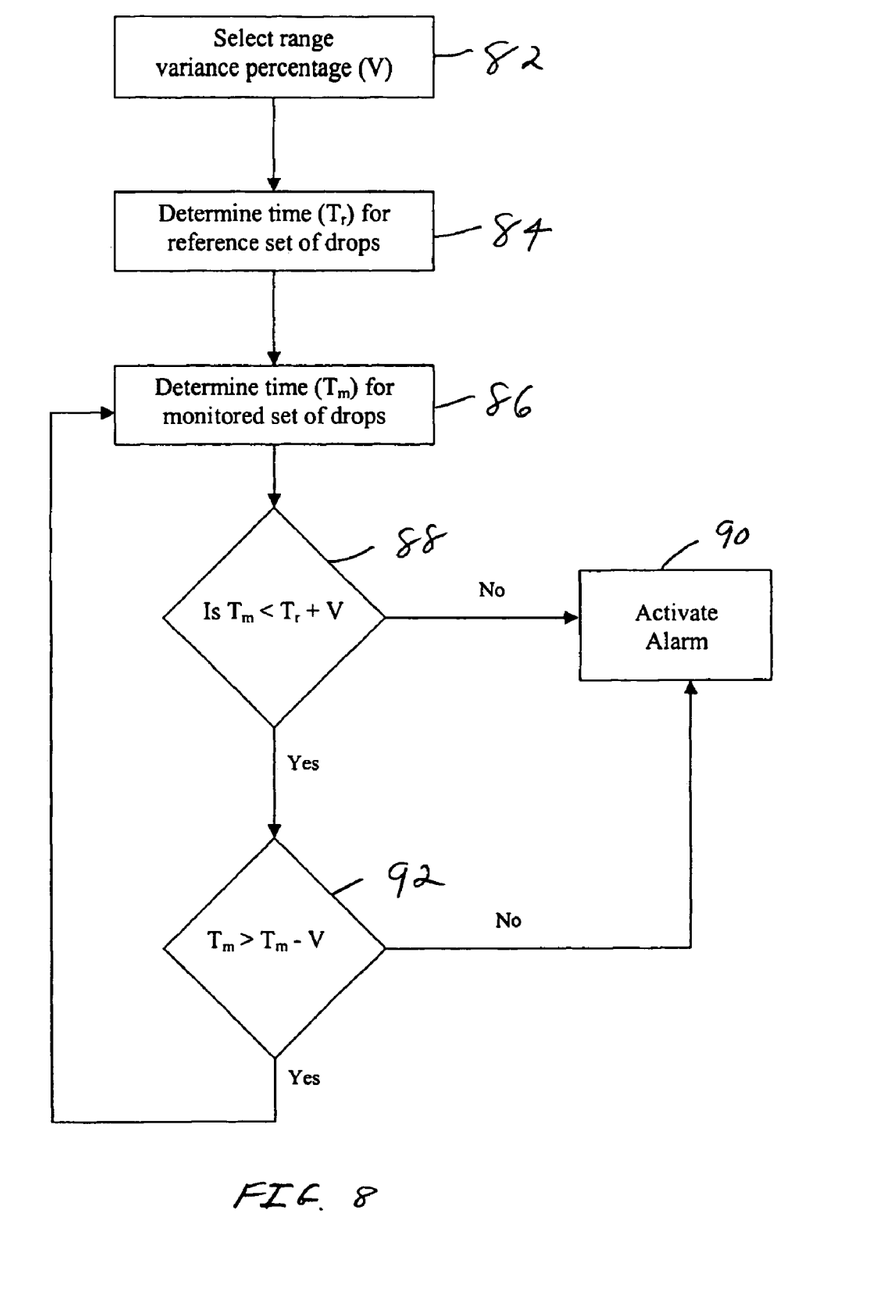
FIG. 8 is a flow chart for the drip rate monitor of the present invention.

Drip rate monitor 10 has a switch 68 for turning drip rate monitor 10 on and off, and a switch 70 for selecting the percentage variance in the drip rate allowed, as is explained in detail in relation to FIG. 8. An LED display 72 is provided to indicate the selected variance percentage. In addition, a plurality of apertures 74 can be provided proximate the location of alarm 26 to ensure adequate sound transfer during an alarm condition.

Figure 7:
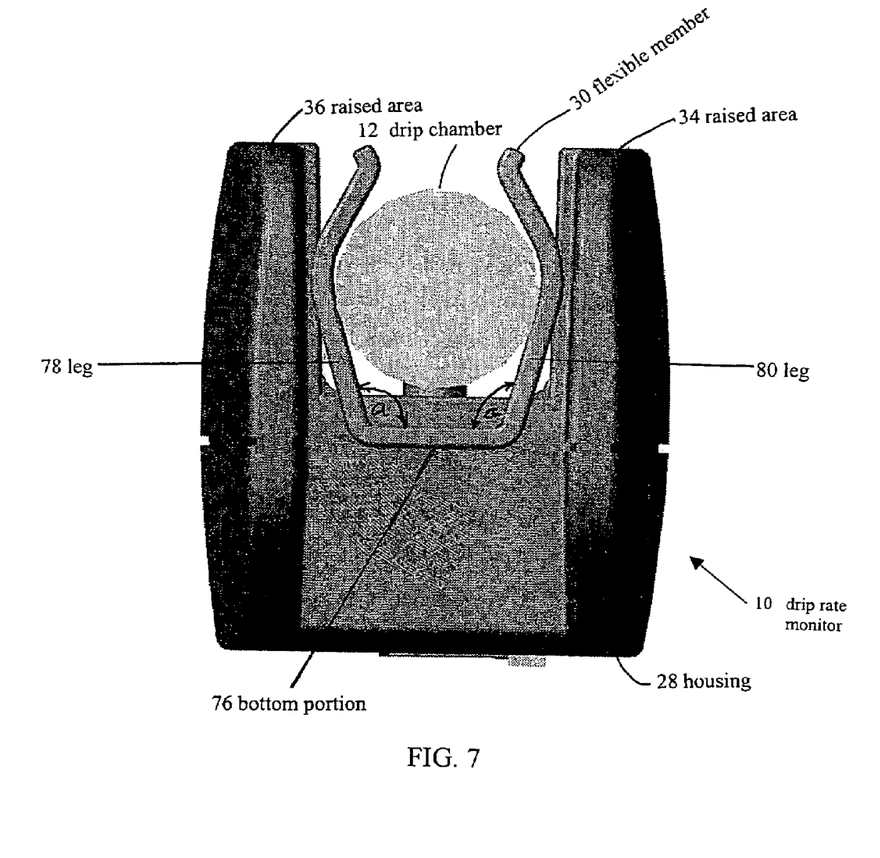
FIG. 7 is an elevational top view of the drip rate monitor shown in FIG. 2.

Referring to FIG. 7, flexible member 30 has a straight bottom portion 76, and two legs, 78 and 80, each extending from an end of bottom portion 76. Flexible member 30 has an opening between legs 78 and 80 opposite bottom portion 76 that is less than the diameter of a micro drip chamber embodiment of drip chamber 12. Legs 78 and 80 have three portions with a first portion attached to said bottom portion and extend outwardly from said bottom portion at an angle "a" that is greater than ninety degrees, a second portion being partially rounded and a third portion extending towards a centerline of said bottom portion.

A flow chart for implementing the present invention is shown in FIG. 8. The steps illustrated in the flow chart of FIG. 8 can be implemented in software and performed by processor 24 as shown in FIG. 1. At step 82 the drip rate variance (V) is selected. Depending upon the embodiment, drip rate monitor 10 can have a preset number of variance percentages to choose from or can be infinitely variable. In one embodiment, the operator can choose either a variance of 12% or 18%, although other appropriate values can be chosen. In step 84 the time ($T_r$), which is the time for the reference set of drops to be detected, is determined. For example, time ($T_r$) can be the time required for infrared detector 22 to detect 8 drops. Steps 82 and 84 can be considered to be the set up mode portion of the process. The actual monitoring of the drip rate starts with step 86 in which processor 24 determines the amount of time ($T_m$) for a monitored set of drops to be detected, i.e., 8 drops in the example above. In steps 88 and 92, processor 24 checks time ($T_m$) to determine is it is within the range of $T_r+V$ and $T_r-V$. If time ($T_m$) is not within the range, step 90 activates alarm 26. If time ($T_m$) is within the range, the process returns to step 86 and is repeated.

It is to be understood that variations and modifications of the present invention can be made without departing from the scope of the invention. It is also to be understood that the scope of the invention is not to be interpreted as limited to the specific embodiments disclosed herein, but only in accordance with the appended claims when read in light of the foregoing disclosure.

What is claimed is:

1. An apparatus for monitoring the drip rate of an infusion fluid being administered by an intravenous infusion set, said apparatus comprising: a housing attachable to a drip chamber; a drop sensor positioned in said housing to detect drops of the infusion fluid being administered by the intravenous infusion set; an alarm; and a processor for determining a first amount of time required for said drop sensor to detect a first set of drops of infusion fluid having a predetermined number of drops, for determining a second amount of time required for said drop sensor to detect a second set of drops of infusion fluid having the predetermined number of drops, for comparing said second amount of time to a range of time having a minimum that is less than the first amount of time and a maximum that is greater than the first amount of time, and for activating said alarm if said second period of time is not within said range of time.

2. An apparatus as recited in claim 1, further comprising a user input device to enable a user to select the range of time from a plurality of ranges of time and wherein said processor uses the range of time selected by the user to determine whether to activate said alarm.

3. An apparatus as recited in claim 1, further comprising a user input device to enable a user to select a percentage and wherein said processor uses the selected percentage to calculate the minimum and maximum times for the range of time.

4. An apparatus as recited in claim 1, wherein said sensor comprises an infrared transmitter and an infrared receiver.

5. A portable apparatus for monitoring the drip rate of an infusion fluid being administered by an intravenous infusion set, said apparatus comprising:
a housing; a flexible member for attaching said housing to a drip chamber of the intravenous infusion set, said member being detachable from said housing; and a drop sensor positioned in said housing for detecting the drops in a drip chamber.

6. An apparatus as recited in claim 5, wherein said housing has an area suitable for holding a battery.

7. An apparatus as recited in claim 5, wherein said member can attach said housing to either a macro drip chamber or a micro drip chamber.

8. An apparatus as recited in claim 7, wherein said member has a straight bottom portion, two legs, each leg extending from an end of the bottom portion and an opening between said legs opposite said bottom portion, said opening being less than the diameter of a micro drip chamber, and said legs having three portions with a first portion attached to said bottom portion and extend outwardly from said bottom portion at an angle that is greater than ninety degrees, a second portion being partially rounded and a third portion extending towards a centerline of said bottom portion.

9. An apparatus as recited in claim 5, further comprising a second member for attaching said housing to an intravenous tube, said second member being detachable from said housing.

10. A method of monitoring the drip rate of an infusion fluid being administered by an intravenous infusion set, said method comprising the steps of: detecting the drops of infusion fluid being administered by the intravenous infusion unit; determining a first amount of time required to detect a first set of drops of infusion fluid having a predetermined number of drops; determining a second amount of time required to detect a second set of drops of infusion fluid having the predetermined number of drops; comparing the second amount of time to a range of time having a minimum that is less than the first amount of time and a maximum that is greater than the first amount of time; and providing an alarm if the second period of time is not within the range of time.

11. A method as recited in claim 10, further comprising the step of selecting a range of time from a plurality of ranges of time.

12. A method as recited in claim 10, further comprising the step of selecting a percentage (x) from a plurality of percentages to determine the range of time by providing a minimum time that is equal to the first amount of time multiplied by the quantity $(1-x)$ and maximum time that is equal to the first amount of time multiplied by the quantity $(1+x)$.

13. A method as recited in claim 10, wherein said detecting step comprises transmitting an infrared light signal into an area through which infusion drops fall and detecting the infrared light signal that passes through the area.

\* \* \* \* \*